US00PP33656P2

(12) United States Plant Patent
Zemzami

(10) Patent No.: US PP33,656 P2
(45) Date of Patent: Nov. 23, 2021

(54) TANGOR TREE NAMED 'SWEET COTT 3'

(50) Latin Name: *Citrus clementina*
Varietal Denomination: Sweet Cott 3

(71) Applicant: Qualiagro SA, Casablanca (MA)

(72) Inventor: Mustapha Zemzami, Kenitra (MA)

(73) Assignee: Qualiagro SA, Casablanca (MA)

( * ) Notice: Subject to any disclaimer, the term of this patent is extended or adjusted under 35 U.S.C. 154(b) by 0 days.

(21) Appl. No.: 17/031,491

(22) Filed: Sep. 24, 2020

(51) Int. Cl.
*A01H 5/08* (2018.01)
*A01H 6/78* (2018.01)

(52) U.S. Cl.
USPC ..... Plt./201

(58) Field of Classification Search
USPC ..... Plt./156, 202, 201
See application file for complete search history.

(56) References Cited

PUBLICATIONS

Bulletin de la Protection des Obtentions Vegetales. 2017. http://www.onssa.gov.ma/images/controle_semences/bulletin-de-protection-des-obtentions-vegetales-n28-septembre-2017.pdf. 12 pages. (Year: 2017).*

* cited by examiner

*Primary Examiner* — Susan McCormick Ewoldt
*Assistant Examiner* — Karen M Redden
(74) *Attorney, Agent, or Firm* — Klarquist Sparkman, LLP

(57) ABSTRACT

A new and distinct tangor tree characterized by less sensitivity to fruit drop due to heat wave, no alternate bearing, very low seed count, low viable pollen, better fruit size, smooth rind, less fruit drop at full maturity and rare *Ceratitis capitata* damage on the fruit.

8 Drawing Sheets

Genus and species: *Citrus clementina* hort. Ex Tanaka x *Citrus reticulata* Blanco.

Variety denomination: 'Sweet Cott 3'.

CROSS-REFERENCES TO RELATED APPLICATIONS

Co-pending U.S. application Ser. No. 17/031,339 (Tangor tree named 'Sweet Cott 2') was developed by the same breeding program.

ORIGIN OF THE INVENTION

The present invention relates to a new and distinct variety of a tangor tree named 'Sweet Cott 3' which was originated by the inventor by gamma irradiating the variety 'AS-2' (unpatented), and selecting for trees having late ripening timeframes, lower seediness, desired organoleptic quality and some other descriptors of interest.

BACKGROUND OF THE INVENTION

The *Citrus* industry is facing tremendous challenges to cope with the recent extensive world-wide plantings of soft *Citrus* that resulted in congestion of market supply due to the narrow maturity windows of conventional varieties that suffer lower sell prices.

To overcome this situation, a breeding program was instituted to generate new varieties of late easy-peeling *Citrus* selections that may expand soft *Citrus* offer beyond traditional maturity time frames. The breeding program targeted creation of new varieties of very late easy peelers with superior agronomical and organoleptic features. Field trials were conducted using shoot-tip grafted and indexed plant material of selected late varieties from our germplasm repository (unpatented). After evaluation, a late maturing tree was identified and was propagated from budwood introduced from Saudi Arabia under the name 'Fun 2 mandarin' which was registered in our repository as Tangor 'AS-2' (unpatented).

In the field trial, trees from 'AS-2' exhibited numerous phenotypical similarities with variety 'SRA 337' (known in USA as 'C54-4-4' or 'Fun' mandarin, which is unpatented) when grown under the same environmental conditions. However, one of the 'AS-2' trees in the trial was noticeably distinct with less vigor of its canopy, its upright growth and a much later maturity (Week 13 to 17) than 'SRA 337' (Week 43 to 52). Budwood of this unique tree was gamma irradiated in 2013 using a Cobal-60 panoramic irradiator in Boukhalef, Tangier, Morocco.

Irradiated budwood was sequentially grafted at a *Citrus* nursery in Kenitra, Morocco on Volkamer lemon root-stock (unpatented) to speed up the growth. The last generation of vegetatively propagated plants was planted in 2015 at the experimental field in Beni Mellal Morocco. Pomological observations started in 2017 with a focus on seediness, time of maturity, organoleptic quality and some other descriptors of interest. 'Sweet Cott 3' and other unique varieties were selected, each having several distinct characteristics making it unique as compared to 'AS-2'.

BRIEF SUMMARY OF THE INVENTION

As evidenced by the following unique combination of characteristics that are outstanding in 'Sweet Cott 3', this new variety is distinct from 'AS-2' variety, as well as from all other varieties of which I am aware. Among several selections, 'Sweet Cott 3' has several distinct characteristics that make it unique as compared to AS-2 including but not limited to:

1. Less sensitivity to fruit drop due to spring heat wave.
2. No alternate bearing even with too late harvest of the previous crop season.
3. Lower seed count in the fruits (2 seed per fruit for 'Sweet Cott 3' versus 19 seed per fruit for 'AS-2') under heavy open field cross-pollination.
4. Low viable pollen as shown by pollen culture on sucrose-Agar medium (12% for 'Sweet Cott 3' compared to more than 60% for 'Nadorcott' variety).
5. Better fruit size (width 68 mm for 'Sweet Cott 3' versus more than 95 mm for 'AS-2').
6. Smooth rind.
7. Less fruit drop at full maturity.
8. Rare *Ceratitis capitata* damage on the fruit of 'Sweet Cott 3'.

'Sweet Cott 3' also has several distinct characteristics from 'Sweet Cott 2', including but not limited to:

1. Earlier ripening time (weeks 11 to 14 for 'Sweet Cott 3' versus weeks 13 to 16 for 'Sweet Cott 2').
2. Fruit seediness (2 seeds per fruit for 'Sweet Cott 3' versus less than 0.3 for 'Sweet Cott 2') under heavy open field cross-pollination.
3. 'Sweet Cott 3' has a greater fruit load with a suitable caliber (less oversize fruits) in comparison with 'Sweet Cott 2'.

Asexual reproduction of this new variety by bud-grafting as performed in the *Citrus* nursery in Kenitra, Morocco, shows that the foregoing and all other characteristics and distinctions come true to form and are established and transmitted through succeeding propagations. Bud-eyes are collected and side grafted on a certified receptive Volkamer lemon root-stock and grown for development under plastic house covered with a layer of anti-insect white screen and a top layer of anti-UV yellow plastic. Each of the progeny exhibits identical characteristics to the original plant. The present invention has not been evaluated under all possible environmental conditions. The phenotype may change with variations in environment without a change in the genotype of the plant.

BRIEF DESCRIPTION OF THE DRAWINGS

The accompanying illustrations show typical specimens of the tree, flowers, and fruit of 'Sweet Cott 3' depicted in color as nearly true as it is reasonably possible to make the same in a color illustration of this character.

DETAILED BOTANICAL DESCRIPTION

The following is a detailed description of the new tangor tree selection 'Sweet Cott 3' with color descriptions using terminology in accordance with The Royal Horticultural Society (London) Color Chart, 4$^{th}$ Edition, (2001), except where ordinary dictionary significance of color is indicated. Observations were made of a 5-year old tree.

Tree:

*Plant diameter.*—325 cm on a 4-year-old tree on *Citrus volkameriana* root-stock.

Figure 2:
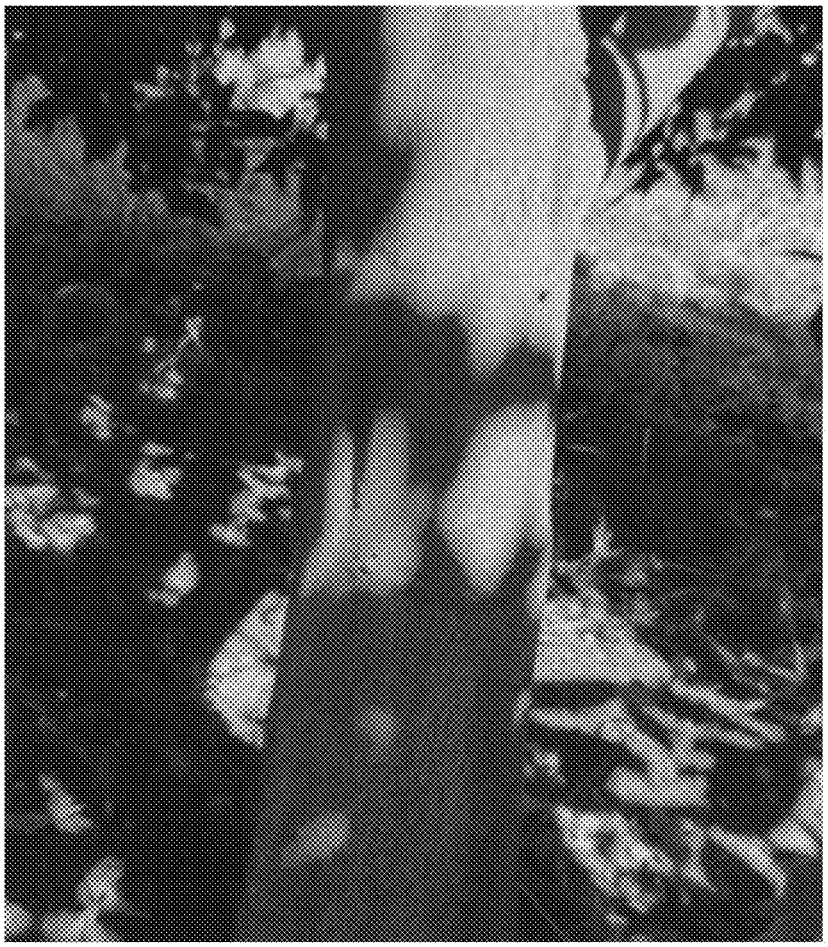
FIG. 2 is a photograph of 'Sweet Cott 3' trunk showing that the stem is strong with smooth bark. It has slight ridges and has an equal diameter with the root-stock.

*Trunk.*—Stem is firm with a smooth bark; it has some ridges and its diameter is equal to the root-stock. See FIG. 2.

Figure 1:
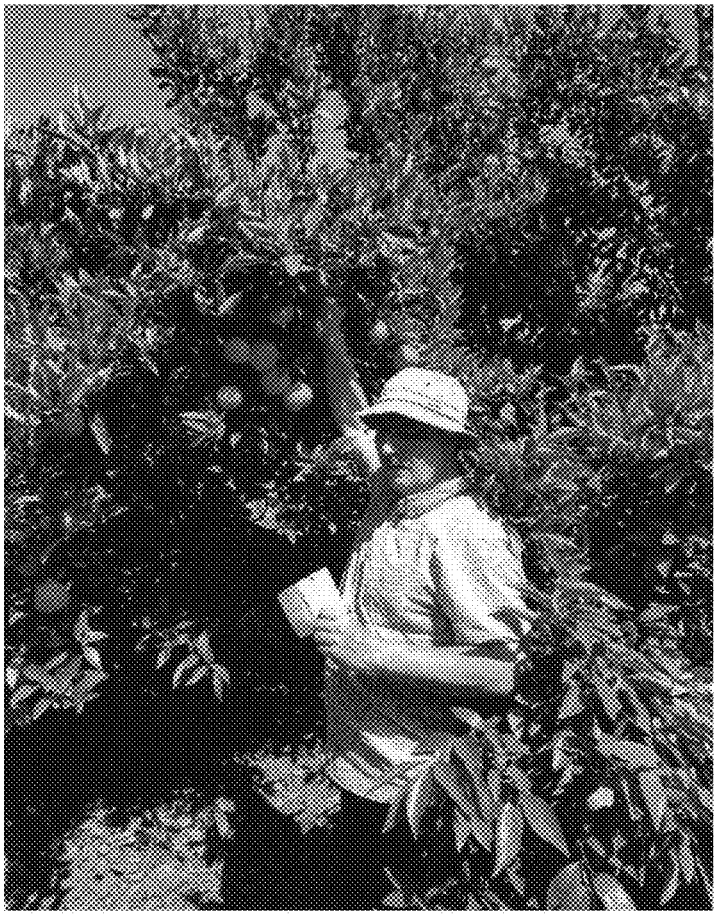
FIG. 1 is a photograph of 'Sweet Cott 3' tree canopy with the upright growth.

*Canopy.*—Moderately vigorous with an ellipsoid shape and an upright growth. The density of branches is medium; their attachment angle is rather narrow. See FIG. 1.

Figure 3:
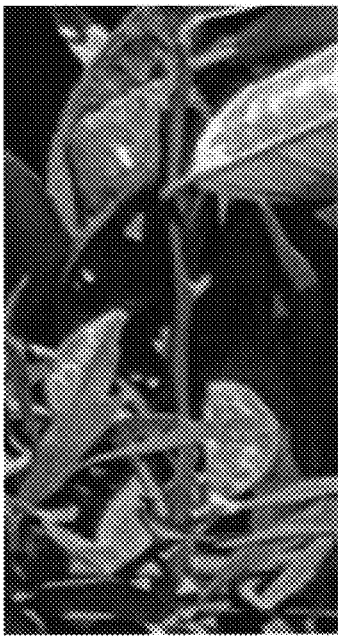
FIG. 3 is a photograph of a 'Sweet Cott 3' first year twig, which is green and glabrous and moderately thick.
Figure 4:
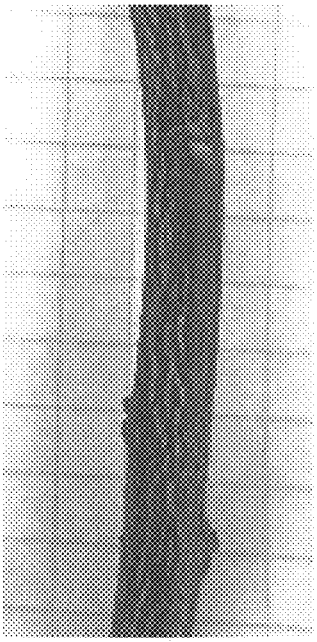
FIG. 4 is a photograph of a 'Sweet Cott 3' second year twig, which is striate.
Figure 5:
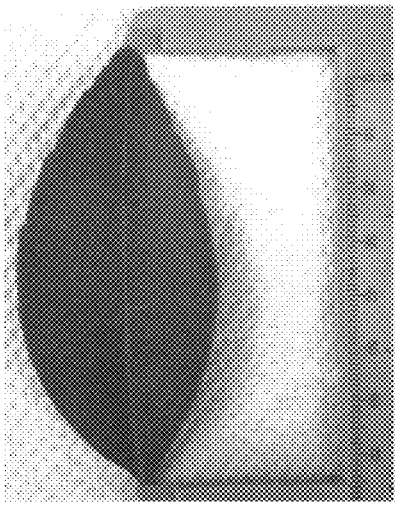
FIG. 5 is a photograph of a 'Sweet Cott 3' leaf, showing elliptic shape.
Figure 6:
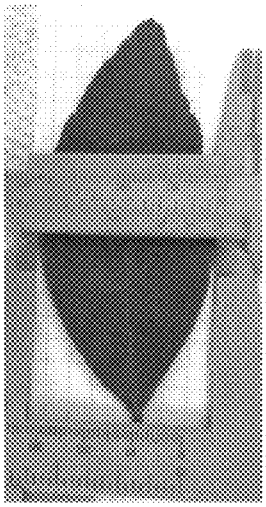
FIG. 6 is a photograph of a 'Sweet Cott 3' leaf, showing apex slightly emarginated.
Figure 7:
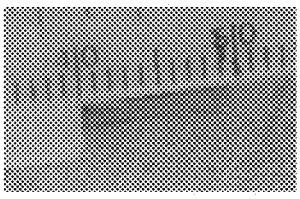
FIG. 7 is a photograph of a 'Sweet Cott 3' petiole, showing it is glabrous with no wings.
Figure 8:
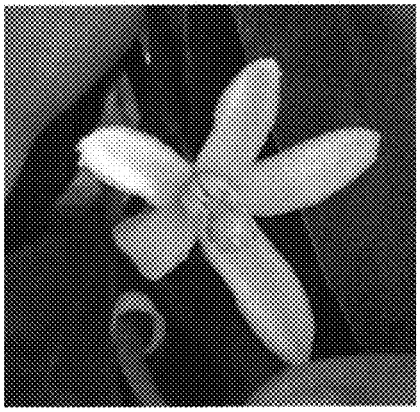
FIGS. 8-10 are photographs of a 'Sweet Cott 3' type 1 flower with one set of petals.
Figure 9:
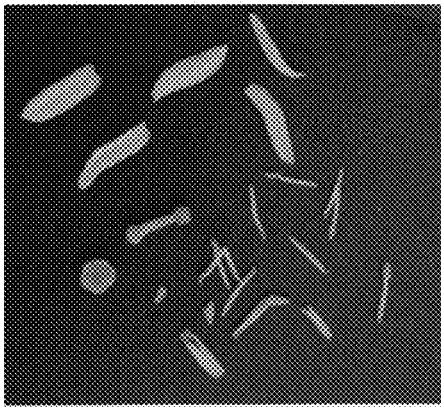
Figure 10:
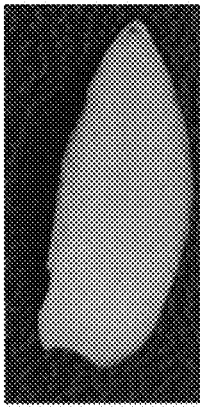
Figure 11:
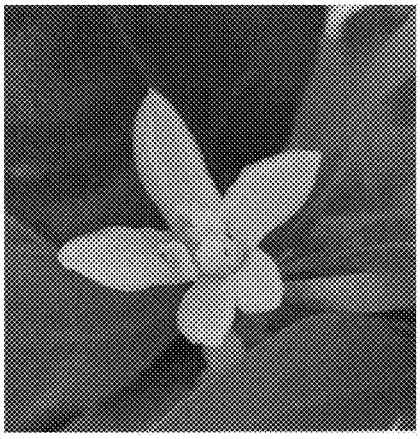
FIGS. 11-13 are photographs of a 'Sweet Cott 3' type 2 flower with two sets of petals, and showing oil glands.
Figure 12:
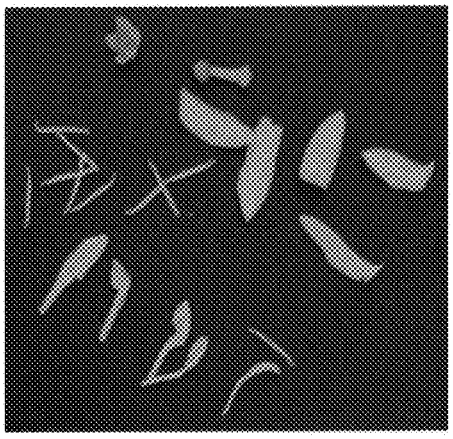
Figure 13:
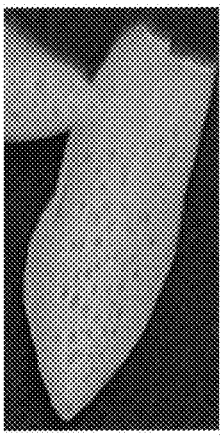
Figure 14:
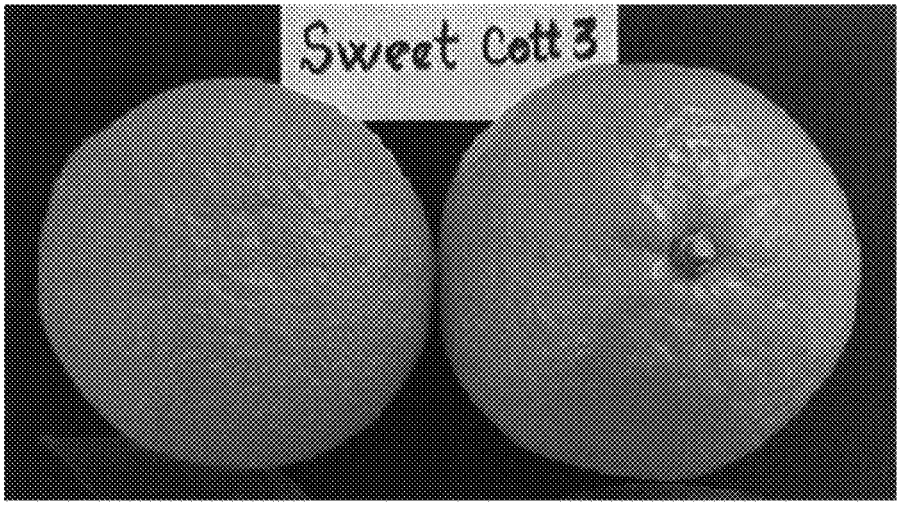
FIG. 14 is a photograph of 'Sweet Cott 3' fruits, with stylar areola and stalk moderate grooves.
Figure 15:
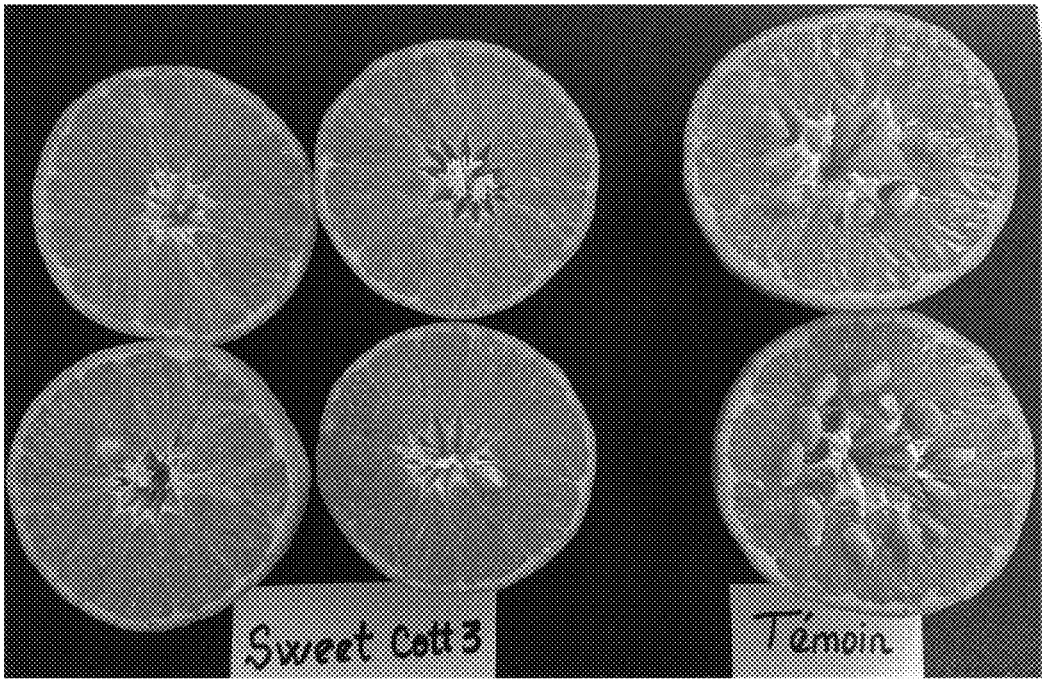
FIG. 15 is a photograph of a comparison between 'Sweet Cott 3' fruits (2 seed/fruit) and 'AS-2' fruit, here indicated as 'Témoin' (19 seeds/fruit).

*Twig.*—First year twig is glabrous, moderately thick and has a green color. See FIG. 3. It becomes subsequently striate with age. See FIG. 4. Thorns are absent and spines are rarely present.

*Growth conditions.*—No particular farming techniques are needed to grow 'Sweet Cott 3'. It does not require any special conditions beside what is usually applied for *Citrus* production.

Stem description:

*Stem length.*—712 mm.

*Diameter.*—105 mm.

*Texture.*—Smooth bark with some ridges.

*Strength.*—Strong.

*Color.*—RHS N 197 A (Light Olive Light Brown).

Leaf description: Unifoliate, plane and elliptic in shape with a glabrous non-winged petiole. The lamina is dotted with medium size oil glands. It has an obtuse apex slightly emarginated and an entire margin but sometimes slightly crenate.

*Shape.*—Elliptic.

*Length.*—86 mm.

*Width.*—34 mm.

*Apex.*—Obtuse with slight emargination.

*Margin.*—Slightly sinuated.

*Texture* (*both surfaces*).—Glabrous.

*Color.*—Adaxial: RHS 137 D (Moderate Yellowish Green); Abaxial: RHS 139 B (Moderate Yellow Green).

*Petiolate or sessile.*—Petiolate. Petiole length: 8 mm. Petiole diameter: 1.12 mm. Petiole color: RHS 146 B (Moderate Yellow Green).

Root description: Grafted on *Citrus volkameriana* rootstock.

Flowers: 'Sweet Cott 3' has 2 types of flowers. Type 2 flower differs from type 1 by having 2 sets of petals. 'Sweet Cott 3' flowers in mid-March and is very productive. It is not prone to alternate bearing in spite of very late harvest of the previous crop.

*Height.*—13.2 mm.

*Diameter.*—9 mm before anthesis.

*Typical date of bloom.*—Mid-March in Beni Mellal, Morocco.

*Number of flowers.*—2 types in singles and clusters.

*Color.*—RHS 155 D (Yellowish White).

*Type 1 flower.*—Set of petals: 1. Pedicel: up to 12 mm in length. Calyx: 5 mm in diameter with 5 sepals arranged in a cup-like structure. Sepal shape is an equilateral triangle with a side length of 4 mm. Color is RHS 137 D (moderate yellowish-Green). Corolla: composed of 5 petals (16.2 mm in length and 5.2 mm in width) arranged in a circle in alternation with the sepals. Stamens: about 15 to 20 in number that seem to be sticking together at their lower part, arranged in a circle. Each stamen has an anther composed of 2 parallel longiform lobs of 2.5 mm in length. The stamens circle the pistil and their anthers are positioned around the stigma at about its same height.

*Type 2 flower.*—Set of petals: 2. The outer set of petals: similar to petals of the type 1 flowers but contains a greater number of oil glands much more conspicuous. The inner set of petals: alternate with the petals of the outer set and differ in their shape as their lower portion is narrow and their upper portion (about $1/3^{rd}$) is large and has a cup-like form which covers the anthers.

Rostellum:

*Length.*—9 mm.

*Thickness.*—1.2 mm.

*Color.*—RHS 154 B (Brilliant Yellowish Green).

Fruit: Fruit attachment to the stalk is strong with no neck. It sometimes shows short radial grooves, which are not always conspicuous.

*Shape.*—Slightly round. Larger than long and has an obloid form.

*Diameter at equatorial level.*—68-80 mm and it is truncate at both stalk and distal parts. The distal end is slightly depressed and has a perceptible smooth areola of round form and medium size.

*Width.*—70 mm.

*Texture.*—Smooth with a slight rough look due to oil glands.

*Color.*—Green fruit — RHS 126 A (medium blue Green); non-dehiscent fruit — RHS N30B (Strong Reddish Orange).

*Fruit rind.*—Dark orange in color RHS N30B and has a thickness of about 2.2 mm shared equally by flavedo and albedo. The rind is dotted with oil glands at a density of 20 small glands per $cm^2$ of about 0.8 mm in diameter, and a larger number of tiny oil glands (about $80/cm^2$). The rind is smooth but with conspicuous oil glands, it has a slight rough look. The albedo is of pinkish white color RHS N155B and shows visible cracking which tends to increase with the progress of ripening.

*Segments.*—11 to 13 which are uniform with a thin membrane.

*Seeds.*—Mean seed count under high cross pollination pressure in mixed bloc with 'Nadorcott', Rough Lemon and Clementine in adjacent rows was 2 seeds per fruit. Seeds are polyembryonic and seed-coat is of yellowish-White color RHS 155 D.

*Fruit axis.*—Hollow with a diameter of about 12 mm.

Figure 16:
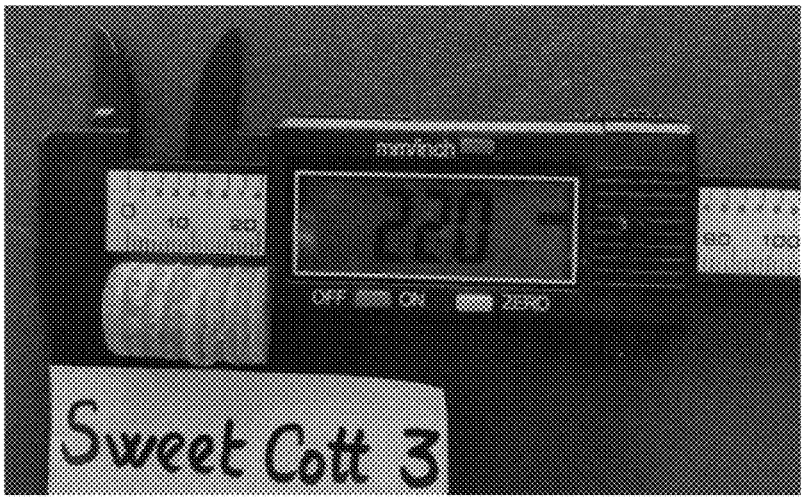
FIG. 16 is a photograph of a 'Sweet Cott 3' fruit peel, with a thickness of 2.2 mm.
Figure 17:
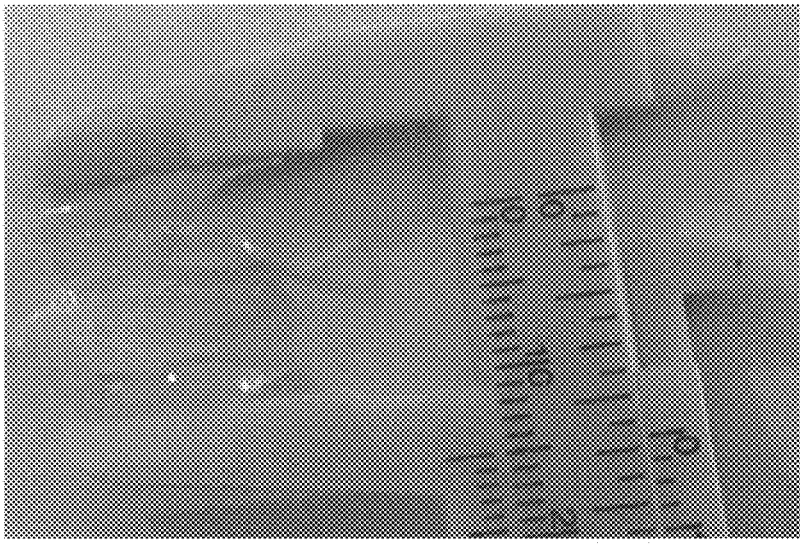
FIG. 17 is a photograph of 'Sweet Cott 3' fruit juice bag width of 3 mm.
Figure 18:
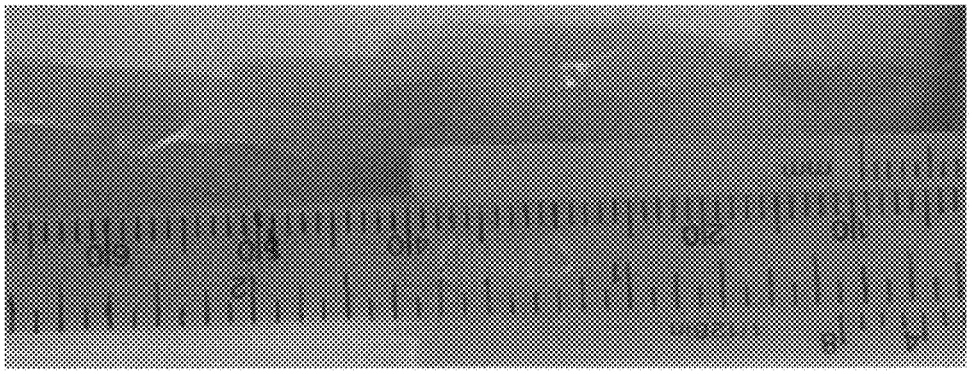
FIG. 18 is a photograph of 'Sweet Cott 3' fruit juice bag length of 12 mm.
Figure 19:
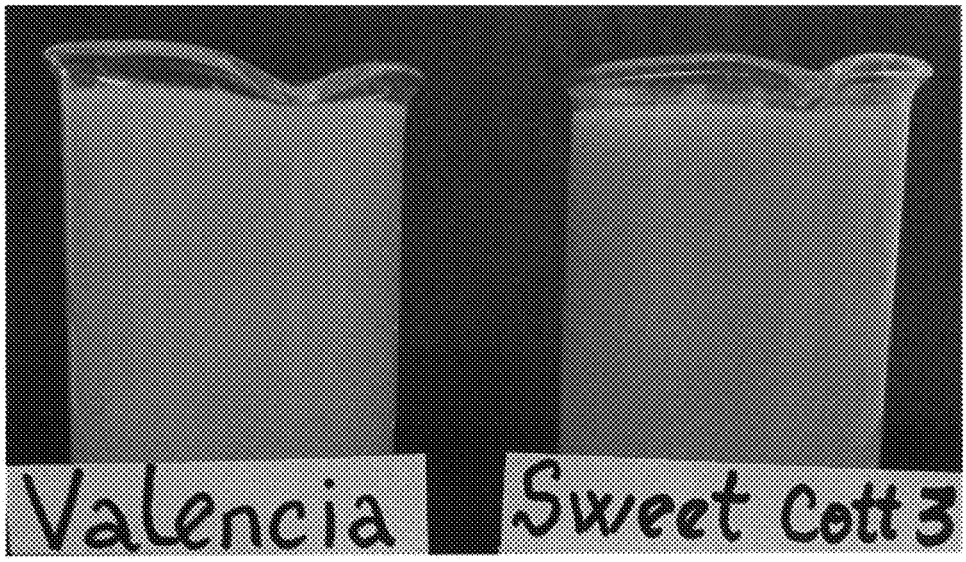
FIG. 19 is a photograph comparing juice from late Valencia and 'Sweet Cott 3' fruit.

*Peel thickness.*—2.2 mm (FIG. 16).

*Stylar.*—A small stylar scar is visible at its center.

*Navel.*—No internal navel is visible when the fruit is peeled.

*Pulp.*—Strong reddish orange color RHS N25B, it is firm and fleshy. Juice vesicles are steady rolls of 10 mm long and 3 mm large. The percentage of juice in the endocarp exceeds 50%, Total Soluble Solids (TSS) varies from 11 to 16% and Titratable Acidity (TA) varies from 12 to 0.75 with maturity progress.

Production: Extrapolation of yield of 'Sweet Cott 3' after 5 yrs post-planting with a spacing of 6 by 2 m will exceed 70 Kg of fruit per tree (>55 000 Kg/Ha).

Tolerance to heat waves: 'Sweet Cott 3' is far more resistant than common varieties that suffer great fruit drops due to mid-spring heat waves which cause heavy losses to *Citrus* when they occur in the Mediterranean Basin.

Tolerance to frost: 'Sweet Cott 3' is more tolerant to frost damage than oranges and clementine. Many days of −2° C. to −4° C. in February did not cause any significant damage as was the case with other varieties.

Resistance to *Ceratitis*: Fruit of 'Sweet Cott 3' appear to not be attractive to the fruit fly, and seldom fruit damage due to *Ceratitis capitate* is observed.

Market use: Fruit of 'Sweet Cott 3' is intended mainly for fresh fruit consumption, but may also serve for fresh juice extraction.

I claim:

1. A new and distinct tangor tree named 'Sweet Cott 3', as herein shown and described.

* * * * *